United States Patent [19]

Faulkner

[11] Patent Number: 4,844,065
[45] Date of Patent: Jul. 4, 1989

[54] INTRAOCULAR LENS INSERTING TOOL AND METHOD

[76] Inventor: Gerald D. Faulkner, 1100 Ward Ave., Ste. 1000, Honolulu, Hi. 96814

[21] Appl. No.: 118,313

[22] Filed: Nov. 6, 1987

[51] Int. Cl.⁴ ............................................ A61B 17/28
[52] U.S. Cl. ..................................... 128/321; 128/354
[58] Field of Search ............ 128/354, 321, 346, 303 R

[56] References Cited

U.S. PATENT DOCUMENTS

| | | | |
|---|---|---|---|
| 611,038 | 9/1898 | Lohman | 604/174 |
| 657,497 | 1/1908 | Cichon | 128/354 |
| 964,181 | 7/1910 | Phesay | 128/354 |
| 1,837,277 | 12/1931 | Lund | 128/321 |
| 2,634,728 | 4/1953 | Dale | 128/354 |
| 4,124,905 | 11/1978 | Clark | 128/303 R |
| 4,190,049 | 2/1980 | Hager et al. | 128/303 R |
| 4,198,980 | 4/1980 | Clark | 128/303 R |
| 4,440,170 | 4/1984 | Golden et al. | 128/321 |
| 4,484,911 | 11/1984 | Berlin et al. | 604/174 |
| 4,508,106 | 4/1985 | Angres | 128/303 R |
| 4,702,244 | 10/1987 | Mazzocco | 128/303 R |
| 4,763,650 | 8/1988 | Hauser | 128/330 |

*Primary Examiner*—John D. Yasko
*Attorney, Agent, or Firm*—Price, Gess & Ubell

[57] ABSTRACT

The invention relates to a method of inserting a deformable intraocular lens and incision forceps relating thereto. A folding forceps and fulcrum forceps are provided for use in readying the deformable intraocular lens for insertion into the eye. The folding forceps are cross action forceps and include handles which are biasely connected so that the handles open jaws for folding and holding the deformable intraocular lenses when pressure is applied to the handles. The jaws which fold and hold the deformable intraocular lens have opposing concave surfaces for receiving the intraocular lens and providing a centrally located wider space adapted to receive the optics portion of the lens and a narrower portion for receipt of the haptics portion of the lens. In use the lens is folded without introducing unnecessary stress fractures into the lens and is securely held in place for introduction into the incision in any eye during surgery and is only released by applying pressure to the handles.

11 Claims, 3 Drawing Sheets

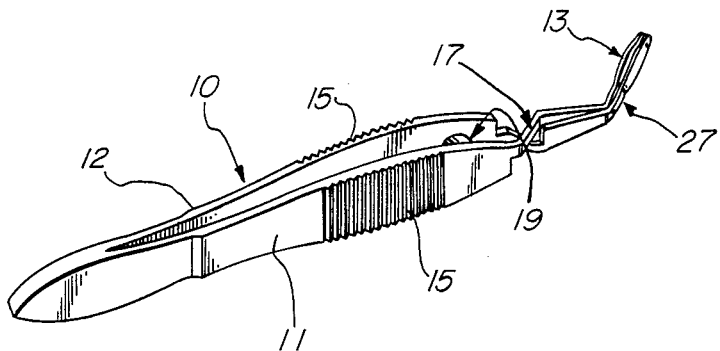
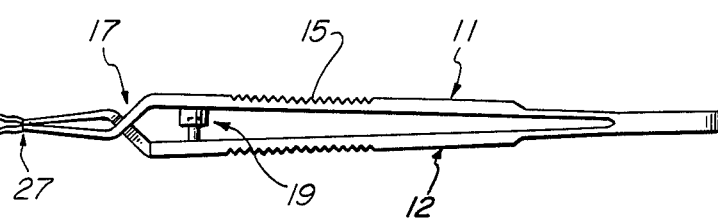
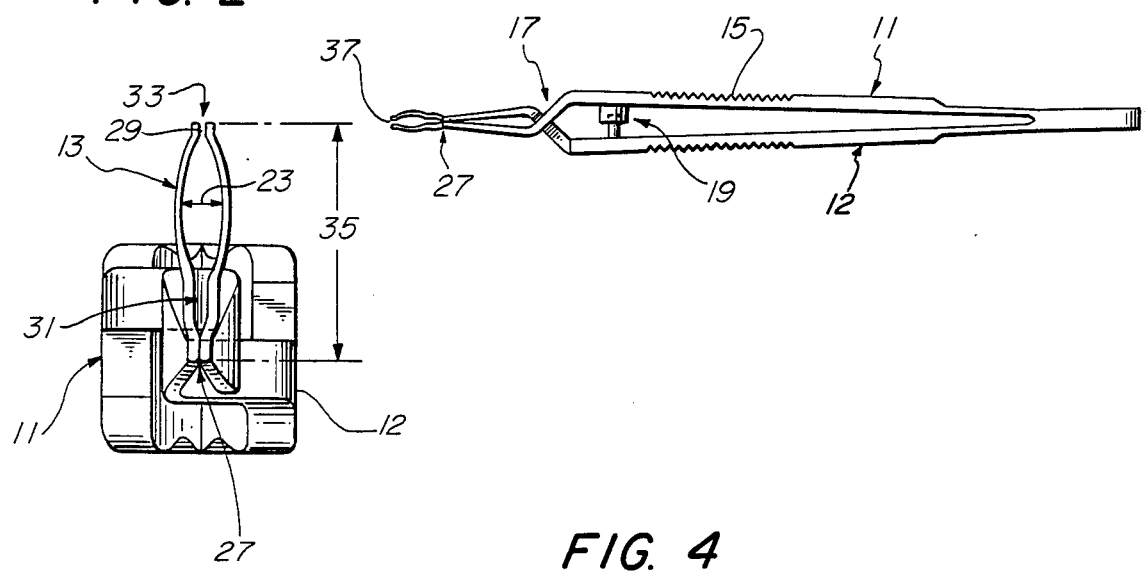
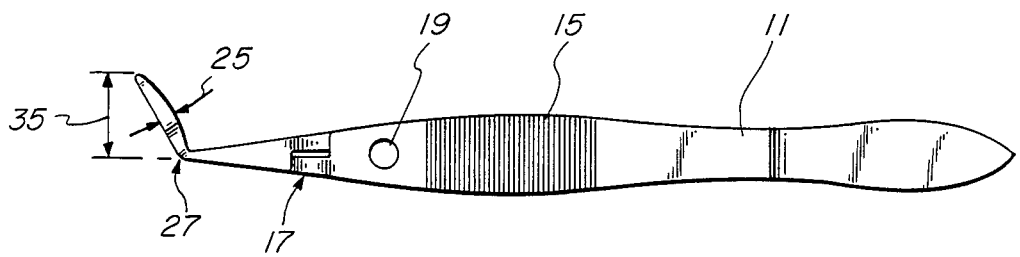

INTRAOCULAR LENS INSERTING TOOL AND METHOD

BACKGROUND OF THE INVENTION

1. Field of the Invention

The present invention provides a method and apparatus for the implantation of an artificial lens implant and more particularly an insertion tool for a flexible intraocular lens.

2. Description of the Prior Art

Intraocular lenses have gained wide acceptance in replacement of the human crystalline lens after a variety of cataract removal procedures. The human crystalline lens is generally recognized to be a transparent structure having a thickness of about 5 millimeters and diameter of about 9 millimeters. The lens is suspended behind the iris by zonular fibers which connect the lens to the ciliary body. A lens capsule surrounds the lens.

Numerous procedures for the removal of cataracts have been developed in which the lens is removed from the eye and replaced by an artificial lens implant. As it is desirable that as small an incision as possible be made in the ocular tissue for both the removal of the lens and the subsequent replacement with an artificial lens, deformable intraocular lenses have recently been developed. Accordingly, the present invention provides an improved method by which a deformable intraocular lens can be inserted into the eye via the small incision.

A number of devices have been developed to facilitate implantation of artificial lenses, for example, U.S. Pat. No. 4,573,998, issued to Mazzocco, describes a number of methods employing such devices. Generally the lens is deformed and constrained to a small volume. Deformable intraocular lenses typically have memory characteristics which enable the lens to be deformed by compressing, rolling, folding or stretching thereof to a diameter of 80% or less of the cross-sectional diameter of the optic part of the lens and yet return to their original configuration full sized and fixed focal length after insertion into the eye. such lenses are often made of silicone or other polymer material.

Various insertion apparatus for use in a deformable lens implantation are known in the prior art. Injection type implantation devices have been used for insertion of the deformable lens into the eye through the small incision. See, for example, FIG. 47 of Mazzocco. In addition, forceps type insertion apparatus have also been used in the prior art, for example, FIGS. 50, 51 and 53 of Mazzocco. Of particular interest to the present invention are the devices and methods calling for forceps-type instruments to grasp the artificial lens and insert it into the eye via a small incision. Some forceps-type devices such as the one described in U.S. Pat. No. 4,198,980, issued to Clark, are designed to interact with the loops and pins of a particular type of intraocular lens design. The forceps described in the Mazzocco patent do not require interaction with loops and pins but rather is capable of grasping any deformable lens. A disadvantage inherent in the above inventions lies in the size of the instrument. The trauma and the chance of additional injury is reduced, if the amount and the size of the instruments inserted into the eye are minimized.

SUMMARY OF THE INVENTION

An object of the present invention is to provide both a tool and method for insertion of an intraocular lens into an eye, which requires a minimal surgical incision in the eye.

A further object of the present invention is to provide such a tool and method which reduces the chance of injury while maneuvering inside the eye.

Also, an object of the present invention is to provide a tool and method of insertion of an intraocular lens which can accommodate a wide variety of deformable artificial lens designs.

The preferred embodiment of the present invention accomplishes these objects by providing a method comprising simultaneously folding and grasping an intraocular lens with a specially designed cross-action forceps, inserting the folded lens into the eye via a small incision and subsequently releasing the pressure of the forceps on the lens while in the eye. This release causes the lens to unfold and position itself within the eye. The forceps are specially curved and angled to accommodate a folded artificial lens and to enhance maneuverability during the operation. The forceps are cross-action so that the pinching pressure is limited to that inherent in the springiness of the device. Moreover, the cross-action configuration prevents an accidental expansion of the forceps while in the eye and According to the invention, folding surgical forceps are provided to fold, hold, place and release the deformable intraocular lens implant within the eye. The folding surgical forceps have a first and second handle which are connected together by a biasing means at one end (for example, a spring). At the other end, first and second jaws are provided for folding and holding a deformable intraocular lens for insertion into the eye through a small incision. The jaws are connected to the handles by crossing bars which connect each jaw to a corresponding handle so that each jaw is connected to the handle on the opposite side. As a result of such cross connection, the jaws will open when the handles are pressed together and will close when the handles are released. The central portion of the jaws are curved (concave) in opposite directions to accommodate the folded optics portion of the implant. The central width of the jaw is wider at this point to accommodate the optics portion which is located in the central portion of the implant and is larger than the haptics portion which is located on the periphery. The dimensions of the space defined between the jaws is determined by the particular deformable implant. The space defined between the jaws should be sufficiently wide so that the folded implant is not unduly stressed by the action of the forceps, but sufficiently narrow to hold the implant securely for introduction into the eye. In use a deformable intraocular lens is placed between the jaws of the folding forceps. The forceps are opened by pressing on the handles to open the jaws for receipt of the deformable intraocular lens. Then the handles are slowly released to fold the deformable lens into the proper position taking care to place the optics portion of the lens within the curved portion of the jaws. When the handles are released, the lens is secured within the folding forceps.

Fulcrum forceps are also provided in accordance with the subject invention. The fulcrum forceps are direct action forceps with smooth, highly polished cylindrical jaws. These forceps are preferably used to hold the implant while folding it in the folding forceps.

In use, a minimum incision will be made into the eye for receipt of the implant. The fulcrum forceps are then used to grasp the implant. The folding forceps will then be used to fold and securely hold the implant for introduction into the eye.

BRIEF DESCRIPTION OF THE DRAWINGS

Other objects and many of the attendant advantages of this invention will be readily appreciated as the same becomes better understood by reference to the following detailed description when considered in conjunction with the accompanying drawings in which like reference numerals designate like parts throughout the figures thereof and wherein:

FIG. 1 is a perspective view of the preferred embodiment of the forceps tool of the present invention;

FIG. 2 is an elevated front view of the forceps tool;

FIG. 3 is a top plan view of the forceps tool;

FIG. 4 is an elevated side view of an embodiment of the present invention;

DETAILED DESCRIPTION OF THE PREFERRED EMBODIMENT

Figure 5:
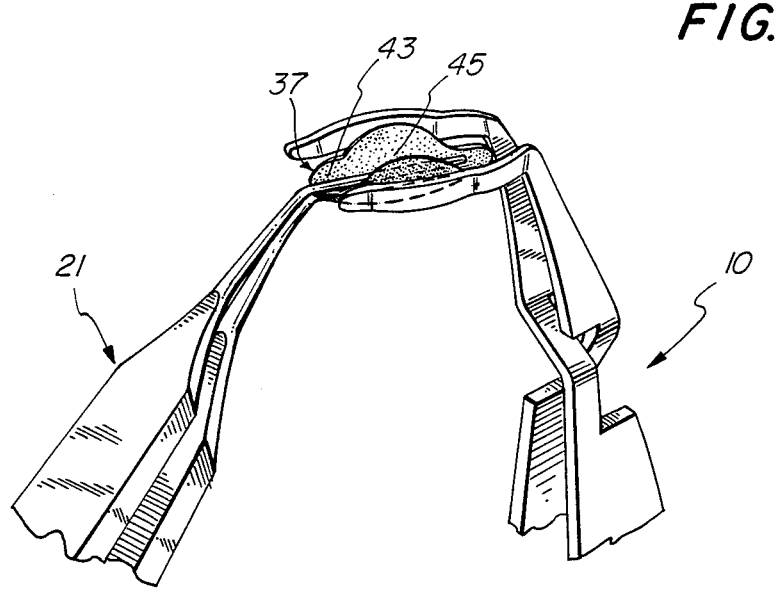
FIG. 5 shows the tool folding an intraocular lens prior to insertion into the eye.
Figure 6:
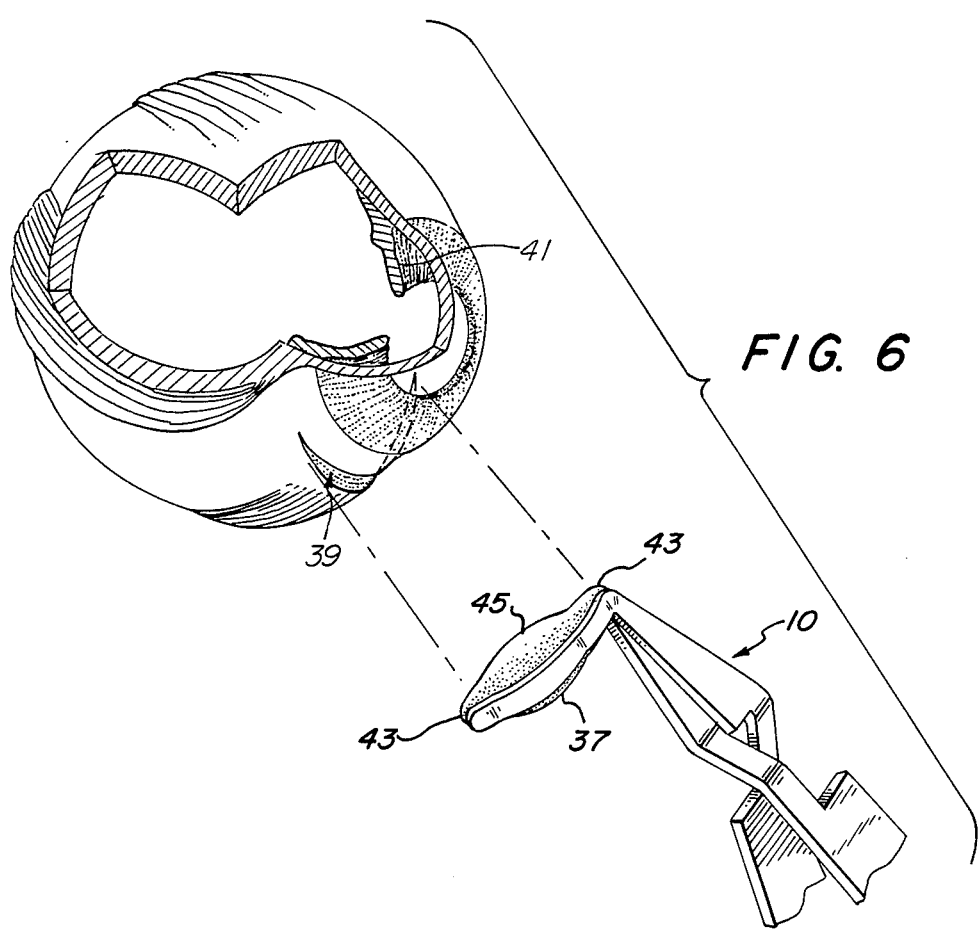
FIG. 6 illustrates the folded implant in the jaws of the forceps tool as the corneal incision is approached.
Figure 7:
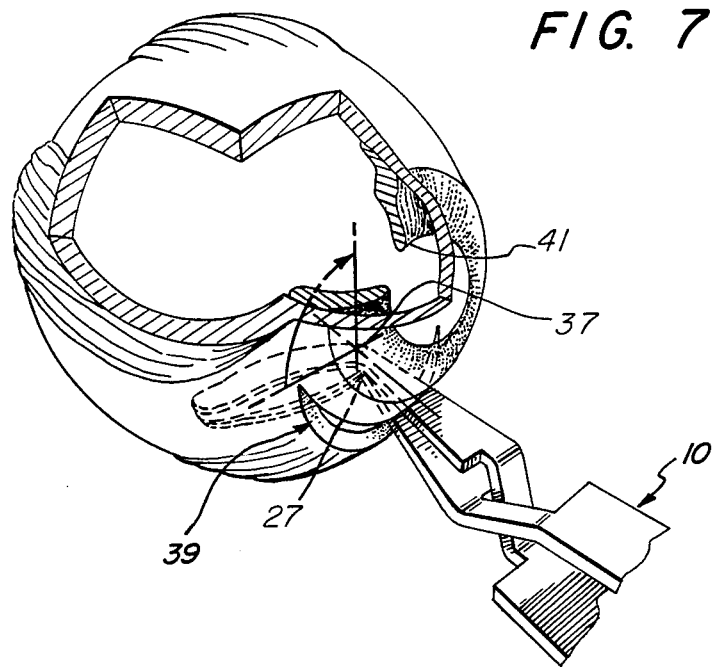
FIG. 7 shows the implant in the eye still within the grasp of the forceps tool.

The following description is provided to enable any person skilled in the medical field relating to intraocular transplants to make and use the present invention and sets forth the best modes contemplated by the inventor of carrying out his invention. Various modifications, however, will remain readily apparent to those skilled in the art since the generic principles of the present invention have been defined herein specifically to provide an improved intraocular lens implant method and tool.

The subject invention provides a method for introduction of a deformable intraocular lens into the eye and surgical apparatus relating thereto. According to the invention, folding forceps and fulcrum forceps are used to conveniently and easily prepare the deformable intraocular lens for implantation without unnecessarily introducing stress fractures into the lens. The folding forceps are conveniently to use and hold the folded implant securely in place until released by the surgeon, thus, reducing the likelihood that the implant will be unintentionally released into the eye.

The folding forceps have biasely connected handles which are cross connected to jaws for holding the handles together and closed when the handles are released. The jaws have opposed concave surfaces for receipt of the intraocular implant. When the jaws are closed the implant is folded and securely held without introducing significant stress fractures into the implant.

Fulcrum forceps are also provided in accordance with the subject invention. The fulcrum forceps are direct action forceps with smooth, highly polished cylindrical jaws. These forceps are preferably used to hold the implant while folding it in the folding forceps.

FIG. 1 is a perspective view of the preferred embodiment of the forcep tool of the present invention. These folding forceps 10 are a cross-action forceps with extension members at one to support ribbon jaws 13 that are designed to hold and release a soft intraocular lens implant. The cross-action handles 11 and 12 are connected at one end to form a handle assembly and are biased strongly enough to maintain foldable implants of a wide range of thicknesses in a folded state within the jaws 13 formed at their respective other ends. A serrated surface 15 can be provided on opposite sides of the handles 11 and 12 to provide a non-slip grip for the surgeon. A cross configuration 17 is placed near the jaws 13. Stop 19 is provided to limit the opening of the forceps jaws 13 to the correct size to fold an implant that is, for example, 6 millimeters wide. The jaws 13 are angled to the cross-action handle at 120° to permit ease of insertion and control. The handles 11 and 12 provide right and left hand members lying in a horizontal plane with a central longitudinal axis. A cross-action handle has several advantages over a direct action handle; the loaded forceps will retain the folded implant without attention; using the spring action of the instrument to fold and hold the implant reduces the possibility of damaging compression force being applied to the implant; the surgeon does not have to maintain any compression force on the forceps when handling the instrument prior to and during insertion, reducing the possibility of losing the folded implant from the forceps; and the release of the implant inside the eye is easier to control. The jaws 13 are ribbons of stainless steel designed to fold the implant over the fulcrum forceps 21, FIG. 5 and to serve as a guide and support for the implant during insertion.

FIG. 2 shows an elevated front view of the jaws of the forceps. The central portion of the right and left jaws are curved in opposite directions to accommodate the folded optic of the implant. The folding forceps preferably have a maximum insertion length of 12 mm. The central width of each jaw 25 is made wider to increase the surface contact area with the implant and to therefore increase the holding friction. This decreases the possibility of damage to the optical surface. The central curve 23 and the increased central jaw width 25 act as dilating and receding wedges to aid insertion and to prevent uncontrolled acceleration into the eye when the widest part passes through the incision. The minimum closed dimension is limited by the meeting of the jaws 13 at 27. This limits compression of the implant and prevents damage or fracture. As this portion of the forceps at 27 comes to lie in the incision when the implant is to be released, the thickness and width are minimized to permit the jaws to open wide enough inside the eye to release the implant. The distal ends 33 of the forceps do not meet when the jaws are closed to reduce the possibility of catching and dragging the distal haptic, iris, and anterior capsule when the forceps are being removed from the eye after release of the implant. The maximum insertion length of the forceps 35 is less than 12 millimeters to reduce the possibility of the tips striking the ciliary body when opened to release the implant. The tips are rounded ad polished to prevent snagging of the posterior lens capsule as the implant is inserted. The narrow proximal 31 and distal 29 space between the jaws is intended to support the haptic portion 43 of some implants which are typically thinner than the optic portion 45.

Figure 8:
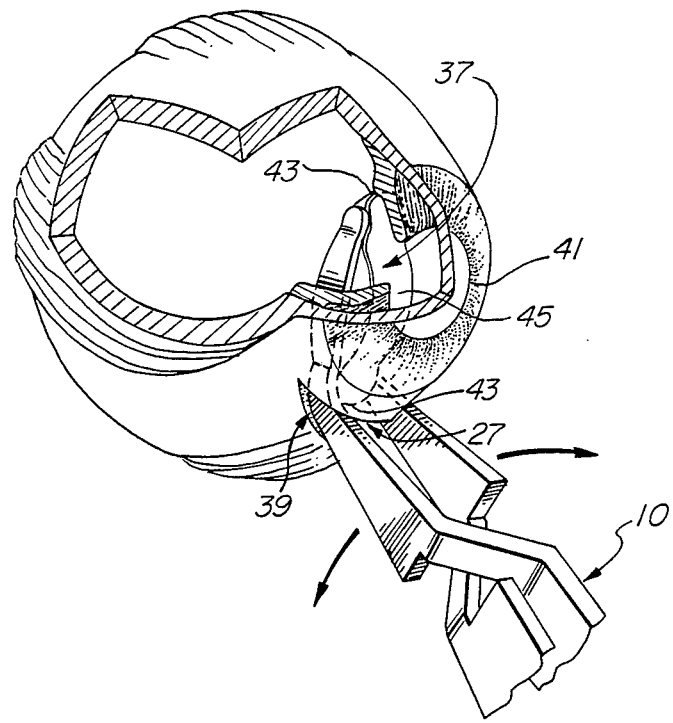
FIG. 8 illustrates the position of the implant and forceps tool just prior to release.

FIG. 5 illustrates the forceps tool folding and grasping the implant 37 prior to insertion into the eye. Minimum incision size will vary with the power of the implant, which determines its thickness. Typically an incision of less than 5 millimeters will accommodate the tool and implant. Fulcrum forceps 21 are used to initially grasp the implant along its axis. The fulcrum forceps can be direct action forceps with smooth highly polished cylindrical jaws used to hold the implant while folding it. Such a design prevents damage to the implant and facilitates easy removal of the forceps from the folded implant. The folding forceps, designated generally as 10, is open to its maximum by compressing the handles until the stop 19 limits the movement of the handle members. The folding forceps are subsequently brought down over the implant with the jaws open to an equal distance from the jaws of the fulcrum forceps. The lens is positioned with the optics portion within the central opening 23 of the folding forceps. The folding jaws are pressed down just until the optic beings to fold and the tension of the handle is released. The fulcrum forceps 21 are removed from the folded implant and set aside. The cornea is lifted with forceps and the lens inserted into the surgical incision. A small amount of inert viscous material can be used to lubricate the implant for insertion but is not required. Gentle pressure is applied to push the lens into the eye and should not be forced. If there is much resistance, the incision should be enlarged. The internal part of the incision must be as wide or wider than the external incision. After the widest portion of the implant has passed through the incision, the forceps are rotated to bring the forceps handle perpendicular to the plane of the iris 41 (implant folded up) as illustrated in FIG. 8, and the leading edge of the forceps is passed carefully beneath the iris or anterior capsule at a six 0'clock position and the lens released by squeezing the handle. The forceps are withdrawn from under the iris with some compression on the handle to keep the tip slightly open so that the under surface of the iris or any portion of the implant is not caught in the forceps. After the tips have cleared the iris, the forceps are allowed to close to the stop and are carefully removed.

It should be understood, of course, that the foregoing relates to a preferred embodiment of the invention and that modifications may be made without departing from the spirit and the scope of the invention as set forth in the following claims.

What is claimed is:

1. Surgical forceps for implanting a deformable intraocular lens having a deformable optic portion and a haptic portion, the forceps comprising:
    a first handle located on the right side of said forceps;
    a second handle located on the left side of said forceps;
    biasing means connecting said first and second handles, said handles spaced apart a predetermined distance while allowing said handles to be selectively pressed together by the user;
    a first jaw located on the right side of said forceps and a second jaw located on the left side of said forceps, and
    connecting means for cross connection of said first jaw to said second handle and said second jaw to said first handle, said jaws having an open position when said handles are pressed together and a closed position when said handles are released; said jaws having opposed concave surfaces such that a concave configuration of said surfaces is described by a line of curvature lying in a longitudinal plane of said jaws, said lines of curvature having an absence of angular portions, said surfaces defining a space therebetween sufficient to deform said intraocular lens along a longitudinal axis to allow placement of said lens through a relatively small incision, and to release said lens in a predetermined internal portion of the eye, said space having a wide contral portion to receive, fold and hold the centrally located optic portion of said lens and a narrow top and bottom portion to receive, fold and hold the generally narrower lens haptics.

2. The forceps according to claim 1 wherein said jaws extend from said handles at an obtuse angle.

3. The forceps of claim 2 wherein said obtuse angle is about 120°.

4. The forceps of claim 3 further comprising a stop located between said first and second handles to prevent compression of said handles and the consequential opening of said jaws more than is necessary to receive an intraocular lens for folding.

5. A surgical tool for inserting a deformable intraocular lens implant into an eye comprising:
    first and second members each having a handle section and a jaw section, the handle section of the first member and the handle section of the second member being flexibly engaged at one end, biased apart and crossing one another near the other end, the jaw section of the first member and the jaw section of the second member angularly extending from the handle sections of the first and second members out of a plane containing the handle sections, the jaw sections being substantially parallel to one another and slightly bowed outward in opposite directions at their centers, the centers of said jaw sections each having a contact surface dimension such that said contact surfaces can contact an optical surface portion of said implant while edge portions of said implant remain out of contact with said contact surfaces; and
    a stop member disposed between the handle sections of the first and second members to limit the maximum separation of the jaw sections.

6. The tool of claim 2 wherein the angle at which the jaw sections extend from the handle sections out of the plane described by the handle sections is about 120°.

7. The tool of claim 2 wherein the jaw sections have proximal and distal ends, the jaw sections being attached to the handle sections at their proximal end, said jaws having a wider central width than the proximal and distal ends, said distal ends not quite touching when the jaws are in their closed position.

8. Cross-action folding medical forceps for folding and grasping deformable intraocular lens and inserting them into an eye via a small incision, comprising:
    (a) two substantially parallel handle members arranged along a longitudinal axis, joined at one end and biased apart;
    (b) an extension member attached respectively to the unjoined ends of the handle members, each extension member crossing the other across the longitudinal axis;
    (c) two parallel jaws each having a proximal end and a distal end and proximately affixed to the extension member at an angle of about 120°, said jaws being curved in opposite directions at their centers to provide a central width that can accomodate an implant optic which has been folded once and generally in half, said distal ends being substantially straight and parallel to one another and not touching when the folding forceps are closed to thereby form a distal space therebetween which has a width that is less than that of said central width, said proximal ends forming a proximal space therebetween which has a width that is less than that of said central width; and (d) a stop member affixed to at least one handle member to limit the maximum separation of the jaws.

9. The folding forceps of claim 8 wherein the jaws are constructed of smooth polished stainless steel.

10. A method of implanting a deformable intraocular lens comprising:

grasping the intraocular lens with fulcrum forceps along its longitudinal axis;

opening a cross action folding forceps by applying a compression force to the handles;

bringing said folding forceps over an optics portion of said intraocular lens;

slowly releasing the folding forceps to simultaneously fold and grasp the intraocular lens on said optics portion, said folding being a single fold which is generally along an axis of said lens, said grasping including the step of placing a haptic portion of said lens in a proximal space and a distal space of said folding forceps;

removing said fulcrum forceps from said intraocular lens;

inserting the lens into the incision in the eye at an angle of from about 30° to 45° to the line of incision;

rotating said folding forceps after the widest part of said intraocular lens has passed through the incision to bring the folding forceps handle assembly perpendicular to the plane of the iris;

maneuvering the leading edge of the forceps beneath the iris, and releasing the intraocular lens by squeezing the handle assembly of said folding forceps.

11. The method of claim 10 wherein said folding forceps comprise:

a first handle located on the right side of said forceps;

a second handle located on the left side of said forceps, the first and second handles forming the handle assembly;

biasing means connecting said first and second handles, said handles spaced apart a predetermined distance while allowing said handles to be selectively pressed together by the user;

a first jaw located on the right side of said forceps and a second jaw located on the left side of said forceps;

connecting means for cross connection of said first jaw to said second handle and said second jaw to said first handle;

pressing the handles together to position said jaws in open position and releasing the handles to provide a closed jaw position, said jaws having opposed concave surfaces to define a space therebetween, said space having a wide central portion to receive, fold and hold of the centrally located optics portion of said lens and a narrow top and bottom portion to fold and hold the generally narrowed lens haptic portion.

* * * * *